United States Patent
Lee et al.

(10) Patent No.: US 9,682,686 B2
(45) Date of Patent: Jun. 20, 2017

(54) RAIN SENSOR HAVING FROST SENSING FUNCTION

(71) Applicants: Hyundai Motor Company, Seoul (KR); Kia Motors Corporation, Seoul (KR)

(72) Inventors: Jin Sang Lee, Seoul (KR); Yong Pyo Hong, Jeollabuk-do (KR); Nam Joon Yoo, Jeollabuk-do (KR); Jong Min Park, Seoul (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 0 days.

(21) Appl. No.: 15/189,165

(22) Filed: Jun. 22, 2016

(65) Prior Publication Data

US 2017/0001600 A1   Jan. 5, 2017

(30) Foreign Application Priority Data

Jul. 3, 2015   (KR) .................. 10-2015-0094995

(51) Int. Cl.
  *G01N 21/55*   (2014.01)
  *B60S 1/08*   (2006.01)
  *G01N 21/552*   (2014.01)

(52) U.S. Cl.
  CPC .......... *B60S 1/0833* (2013.01); *G01N 21/552* (2013.01); *G01N 2201/0636* (2013.01)

(58) Field of Classification Search
  CPC ........... G01N 21/552; G01N 2201/061; G01N 2201/0636; G01N 2201/068
  See application file for complete search history.

(56) References Cited

U.S. PATENT DOCUMENTS

| | | | | |
|---|---|---|---|---|
| 5,436,060 A | * | 7/1995 | Saurer | B32B 17/10036 310/322 |
| 5,661,303 A | * | 8/1997 | Teder | G01N 21/43 250/227.25 |
| 2003/0131613 A1 | * | 7/2003 | Mardberg | B60H 1/00785 62/155 |

FOREIGN PATENT DOCUMENTS

| | | |
|---|---|---|
| JP | H09-257952 A | 10/1997 |
| JP | H1137925 A | 2/1999 |
| JP | 3536738 B2 | 6/2004 |
| JP | 2007033153 A * | 2/2007 |
| KR | 10-0229772 B1 | 11/1999 |
| KR | 2020000010174 | 6/2000 |
| KR | 2009-0111770 A | 10/2009 |
| KR | 2009-0129071 A | 12/2009 |
| KR | 2010-0081094 A | 7/2010 |
| KR | 2011-0010849 A | 2/2011 |
| KR | 2011-0068307 A | 6/2011 |

(Continued)

*Primary Examiner* — Michael P Stafira
(74) *Attorney, Agent, or Firm* — Mintz Levin Cohn Ferris Glovsky and Popeo, P.C.; Peter F. Corless

(57) ABSTRACT

A rain sensor has a frost sensing function, and is attached to a windshield glass of a vehicle. The frost sensor includes a casing provided with a frost sensing region formed by recessing a part of the casing to contact indoor air; a light emitting unit that emits light such that the light is incident on the windshield glass; a light receiving unit that receives the light emitted from the light emitting unit and reflected from the windshield glass and the frost sensing region; and a control unit that outputs the light received by the light receiving unit as a control signal and activates a wiper and an air conditioner of the vehicle.

7 Claims, 7 Drawing Sheets

(56) References Cited

FOREIGN PATENT DOCUMENTS

WO 9535493 A1 12/1995
WO WO 2015/182803 * 12/2015

* cited by examiner

RAIN SENSOR HAVING FROST SENSING FUNCTION

CROSS-REFERENCE(S) TO RELATED APPLICATION

This application claims under 35 U.S.C. §119(a) the benefit of Korean Patent Application No. 10-2015-0094995 filed on Jul. 3, 2015, the entire contents of which are incorporated herein by reference.

BACKGROUND (a) Field of the Invention

The present invention relates to a rain sensor having a frost sensing function, more particularly, to a rain sensor that is attached to a windshield glass of a vehicle to detect raindrops and frost on the surface of the glass and output signals to control a wiper and an air conditioning system of the vehicle depending on types and amounts of substances detected and a drop cycle of raindrops.

(b) Description of the Related Art

In certain rain-sensing wiper systems, when a rain sensor provided in a vehicle detects raindrops and foreign matter on a windshield glass of a vehicle, a control signal is output to operate a wiper of the vehicle so that raindrops and foreign matter on the windshield glass of the vehicle are removed.

However, in cold weather conditions, frost is frequently formed on the interior side surface of the windshield glass of the vehicle due to a temperature difference between the interior and exterior of the vehicle, which may obstruct the driver's view. However, current systems lack a function to remove the frost in a convenient way.

That is, although the driver can remove the frost through an air conditioning system such as a heater and/or a heating wire, there is inconvenience in that the driver manually operates the air conditioning system every time because typically once the frost starts to be generated, the frost continues to be generated even after being removed.

Therefore, it is desirable to provide a rain sensor having a frost sensing function that can assist in driving the vehicle in such a manner that the frost sensing function is added to the rain sensor to detect rainfall and/or generation of frost so as to automatically operate the air conditioning system.

On the other hand, regarding the technology for removing the frost generated on the glass of the vehicle, Korean Laid-Open Patent Publication No. 10-2011-0068307 ("the '307 Publication") discloses an apparatus and method for removing frost from the window of a vehicle, and Korean Patent Publication No. 10-0229772 ("the '772 Publication") discloses a device for generating a voice alarm upon detecting ice on a windshield glass.

In the '307 Publication, if an outdoor air temperature detected by an outdoor air sensor and the type of current-set heating modes fulfill a predetermined determination condition, a value of flow voltage corresponding to the current outdoor air temperature is transmitted automatically to a drive unit of a blower, and ultimately the frost can be removed through flow rate and discharge intensity of air discharged from a heater.

In the '772 Publication, when an engine of a vehicle does not start, values detected by a windshield glass weight sensor and an outdoor air temperature sensor are analyzed, and if it is determined that ice exists on the windshield glass, an air conditioning system is activated and then a voice message of the current situation is output. That is, if the weight of the windshield glass is increased and the outdoor air temperature corresponds to an ice formation temperature, the air conditioning system is activated such that the ice on the windshield glass can be removed.

The above-described publications each disclose removing frost by use of an outdoor air temperature sensor, which has the possibility of malfunctioning due to an error of temperature prediction and non-uniformity of temperature distribution.

Therefore, it is desirable to develop a technology that can directly detect frost such that both rainfall and/or generation of frost can be detected, rather than by utilizing a method for predicting generation of frost through an outdoor air temperature and sensing the frost.

The above information disclosed in this Background section is only for enhancement of understanding of the background of the invention and therefore it may contain information that does not form the prior art that is already known in this country to a person of ordinary skill in the art.

SUMMARY

An object of the present invention is to provide a rain sensor having a frost sensing function, which is attached to a windshield glass of a vehicle and capable of sensing both raindrops and frost on the surface of the windshield glass, where the rain sensor includes: a casing having a frost sensing region formed by recessing a part of the casing to contact indoor air of the vehicle; a light emitting unit for emitting light such that the light is incident on the windshield glass; a light receiving unit for receiving light emitted from the light emitting unit and reflected from the windshield glass and the frost sensing region; and a control unit for outputting the light received by the light receiving unit as a control signal and activating a wiper and an air conditioning system of the vehicle.

A rain sensor having a frost sensing function according to an embodiment of the present invention for accomplishing the above object includes a casing, a light emitting unit, a light receiving unit, and a control unit, and is attached to a windshield glass of a vehicle and capable of sensing raindrops falling on the windshield glass and frost generated on its interior side surface, where the casing is provided with a frost sensing region formed by recessing a part of the surface thereof which is attached to the windshield glass to contact indoor air of the vehicle; the light emitting unit emits light to the windshield glass; the light receiving unit receives the light emitted from the light emitting unit and totally reflected from the windshield glass and the frost sensing region, and outputs signals for the received light; and the control unit analyzes the signals output from the light receiving unit and then outputs a control signal for controlling a wiper and an air conditioning system of the vehicle depending on the condition of the detected raindrops and frost.

As the rain sensor having frost sensing function according to an embodiment of the present invention is attached to a windshield glass of a vehicle to detect raindrops and frost on the surface of the windshield glass and output signals to control a wiper and an air conditioning system of a vehicle depending on types and amounts of substances detected, and a cycle of raindrops, it has a remarkable effect of minimizing an unnecessary operation of a wiper and an air conditioning system.

In addition, the present invention also has a remarkable effect that no additional cost is incurred because the configuration of a rain sensor is modified to detect frost and thus no separate frost sensing sensor is required.

Other aspects and preferred embodiments of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
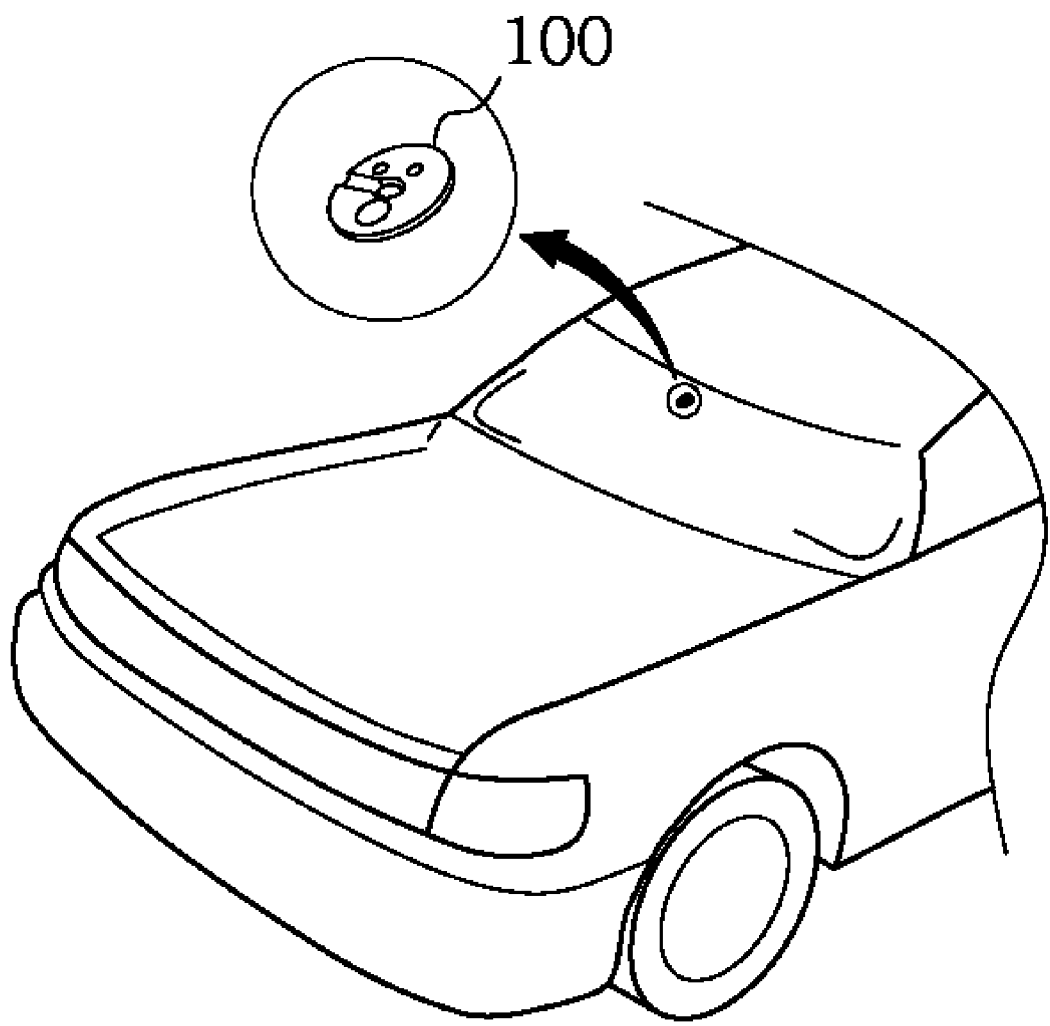
FIG. 1 is a view illustrating an example of a rain sensor having a frost sensing function attached to a vehicle, according to an embodiment of the present invention.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present invention may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

It should be understood that terms or words used in the specification and the appended claims should not be construed as being limited to commonly employed meanings or dictionary definitions, but interpreted based on meanings and concepts corresponding to the technical idea of the invention, on the basis of the principle that inventors are allowed to define terms appropriately for the best explanation of their invention.

Therefore, embodiments described herein and configurations illustrated in drawings are just preferable examples of the invention, but not cover all of the technical idea of the invention, so it should be understood that various equivalents and modifications could be made thereto without departing from the spirit and scope of the invention.

The present invention relates to a rain sensor having frost sensing function, which is attached to a windshield glass of a vehicle to detect raindrops and frost on the surface of the glass and output signals to control a wiper and an air conditioning system of the vehicle depending on types and amounts of substances detected and a drop cycle of raindrops.

An exemplary example that a rain sensor having frost sensing function according to an embodiment of the present invention is attached to a windshield glass of a vehicle will be described with reference to FIG. 1 of the accompanying drawings.

FIG. 1 illustrates an example of a rain sensor having a frost sensing function, attached to a vehicle, according to an embodiment of the present invention.

As shown in FIG. 1, a rain sensor 100 is attached to a windshield glass of a vehicle, but the scope of the invention is not limited or narrowed by the drawings. The rain sensor according to present invention may be attached to any glass equipped with a wiper among different types of glass of a vehicle (e.g. rear glass), as well as the windshield glass of the vehicle. As used herein, the term "windshield glass" refers to the front windshield of a vehicle, or any other glass surface of the vehicle that may receive a wiper.

In particular, since the rain sensor 100 is attached to the windshield glass, it may be designed to conform to the curvature of a surface of the windshield glass. However, as the rain sensor 100 according to the present invention is designed to be compact, it can be used by being attached to the windshield glass without being designed to conform to the curvature of the surface of the windshield glass.

Figure 2:
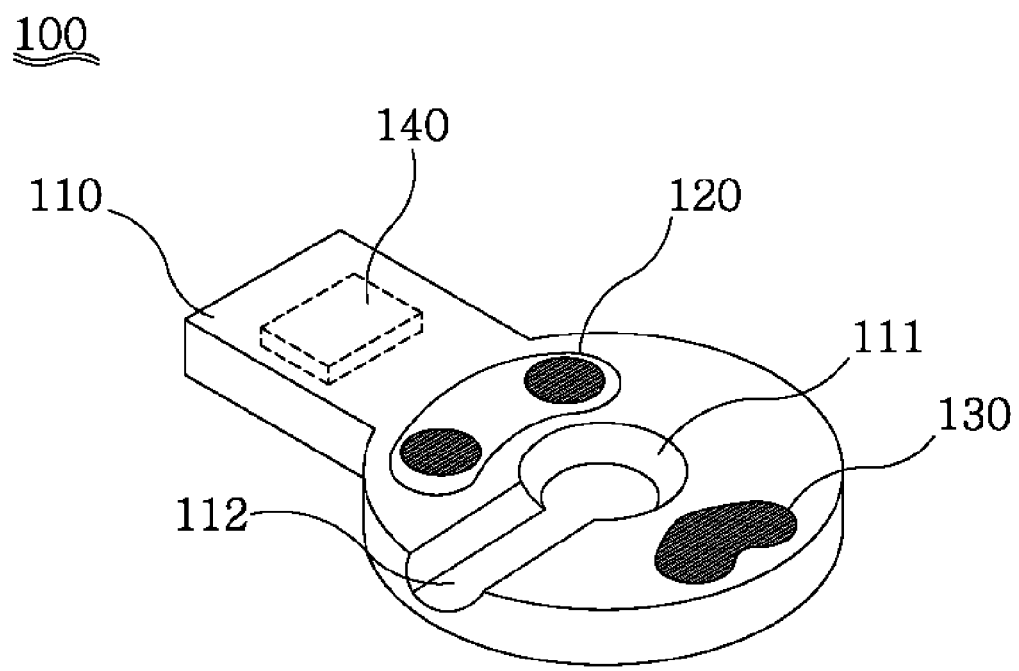
FIG. 2 is a schematic view illustrating main elements of the rain sensor having the frost sensing function according to an embodiment of the present invention.

FIG. 2 schematically illustrates main elements of the rain sensor having the frost sensing function according to an embodiment of the present invention.

As shown in FIG. 2, the rain sensor 100 may include a casing 110, a light emitting unit 120, a light receiving unit 130, and a control unit 140.

The casing 110 protects internal components of the rain sensor 100 and one side surface thereof is attached to the windshield glass of the vehicle 10. The casing 110 comprises a frost sensing region 111 and an air passage 112.

The frost sensing region 111 is formed with a space that may be formed by recessing a part of the surface of the casing 110, which is attached to the windshield glass, i.e., a space in which frost can be generated on the windshield glass positioned at the frost sensing region 111.

The air passage 112 is formed by recessing the same surface as the frost sensing region 111 such that indoor air can be introduced into the frost sensing region 111, and connects the interior of the vehicle 10 and the frost sensing region 111.

The light emitting unit 120 is configured to emit light, the light receiving unit 130 receives the light emitted from the light emitting unit 120 and outputs the received light as a signal, and the control unit 140 is installed in the rain sensor 100, and analyzes and determines the signal output from the light receiving unit 130 and then outputs control signals for controlling a wiper and an air conditioning system of the vehicle 10.

In this case, it is preferable that the frost sensing region 111, the light emitting unit 120 and light receiving unit 130 of the rain sensor 100 according to an embodiment of the present invention are provided at a position where the light emitted from the light emitting unit 120 can be totally reflected from the windshield glass and the frost sensing region 111 and then received by the light receiving unit 130.

Figure 3:
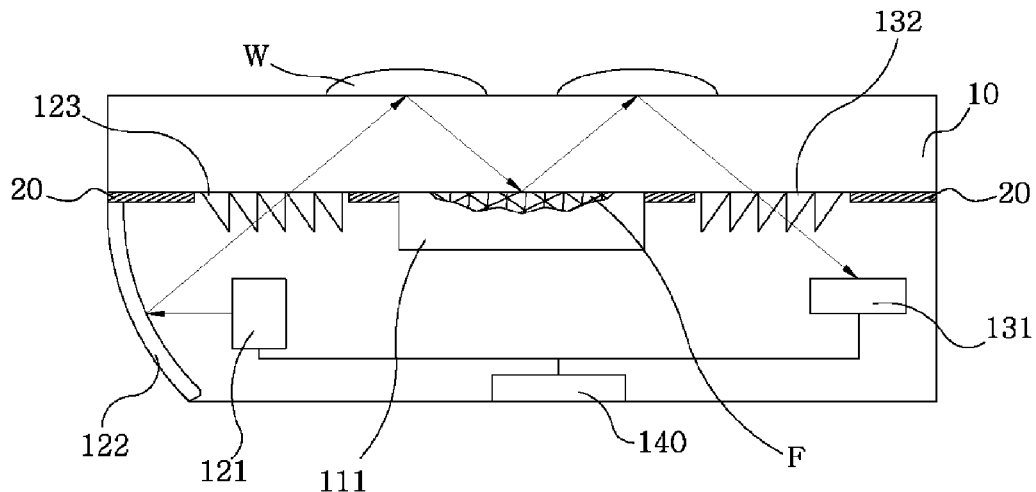
FIG. 3 is a schematic view showing a movement path of light according to an internal configuration and operation of the rain sensor having the frost sensing function according to an embodiment of the present invention.

FIG. 3 illustrates schematically a movement path of light according to an internal configuration and operation of the rain sensor having the frost sensing function according to an embodiment of the present invention.

As shown in FIG. 3, the rain sensor 100 is attached to the windshield glass with an adhesive surface 20 interposed and bonded therebetween to detect raindrops falling on the windshield glass. In this case, substances falling on the windshield glass are not only raindrops but also any substance similar to raindrops.

Most preferably, the adhesive surface 20 is bonded by using silicon adhesives.

In addition, according to FIG. 3, the rain sensor 100 may include the frost sensing region 111, a light emitting module 121, a light emitting parabolic mirror module 122, a light emitting saw-toothed rotational prism set 123, a light receiving module 131, a light receiving saw-toothed rotational prism set 132, and the control unit 140.

The frost sensing region 111 is formed by recessing a partial surface of the rain sensor 100, which is attached to the windshield glass, such that frost F generated on the interior side surface of the windshield glass can be detected. Accordingly, since the frost sensing region 111 can contact the indoor air, frost F can be formed on the windshield glass positioned at the frost sensing region 111.

The light emitting unit 120 shown in FIG. 2 may include the light emitting module 121 for emitting light, the light emitting parabolic mirror module 122, and the light emitting saw-toothed rotational prism set 123.

The light emitting module 121 is configured to emit light, wherein although it is possible for the light emitting module to employ various types of light sources, it is preferable to employ an infrared ray light source. In addition, the light emitting module 121 is configured to emit light to the light emitting parabolic mirror module 122.

In addition, when the light emitting module 121 is made up of two or more modules depending on design conditions of the present invention, such light emitting modules may be designed to emit light of a different wavelength region respectively such that the light receiving unit 130 can distinguish light emitted from the two or more light emitting modules 121.

The light emitting parabolic mirror module 122 may be configured to have a reflection surface of a paraboloid shape as shown in FIG. 3 in order to allow the light emitted from the light emitting module 121 to be incident to the windshield glass. In general, light with a parallel wavelength may be concentrated through the paraboloid surface. By applying such a principle conversely to the rain sensor 100 according to the present invention, the rain sensor may be configured in such a manner that the light emitted from the light emitting module 121 can be reflected in parallel through the light emitting parabolic mirror module 122.

Therefore, the light emitting parabolic mirror module 122 is preferably designed to have curvature of the paraboloid that allows the light emitted from the light emitting module 121 to be reflected in parallel.

The light emitting saw-toothed rotational prism set 123 is configured to transmit the light reflected from the light emitting parabolic mirror module 122.

The light emitting saw-toothed rotational prism set 123 may be configured such that prisms that can maintain the parallel state of light reflected from the light emitting parabolic mirror module 122 are projected in an inner direction.

Therefore, it is possible to maintain the parallel status and an incident angle of the light reflected from the light emitting parabolic mirror module 122 through the light emitting saw-toothed rotational prism set 123.

In addition, since the light emitting module 121 can be made up of two or modules depending on design conditions of the present invention, the light emitting saw-toothed rotational prism set 123 may be configured to rotate (or control) the direction of the prism such that the light emitted from each of the light emitting modules 121 can be received by a single light receiving module 131. Here, the 'rotate' means 'control of a direction' rather than 'turning about an axis.'

Further, the light emitted from the light emitting module 121 is utilized in sensing raindrops W and frost F, wherein the raindrops W and the frost F can be detected based on an amount of the light totally reflected from the glass of the vehicle 10 and the frost sensing region 111. At this time, in order for the light to be totally reflected through a specific medium, the light must be incident at an angle exceeding a critical angle at which total reflection occurs. The total reflection occurs when light travels from a medium of high refractive index to a medium of low refractive index, and when light incident on a medium reaches an incident angle equal to or greater than a predetermined angle, a phenomenon that the light cannot come out of the medium occurs, wherein the predetermined angle is referred to as a critical angle.

In the present invention, the light emitting saw-toothed rotational prism set 123 controls an angle of light such that light being transmitted can be incident on the windshield glass at an angle allowing total reflection.

In general, it is known that the refractive index of glass of vehicles is 1.5 to 1.51 and the reflective index of air is 1. In order to estimate the critical angle of the glass of the vehicle 10 based on values of such reflective indexes, the following equation is used.

$$\theta_{critical\ angle} = \arcsin\left(\frac{n_2}{n_1}\right),\ (\text{where},\ n_1 > n_2)\qquad\text{Equation 1}$$

Where $n_1$ indicates the refractive index of glass of vehicles and $n_2$ indicates the refractive index of air. Accordingly, the critical angle obtained by using Equation 1 above is about 41.4 degrees. The light transmitted through the light emitting parabolic mirror module 122 is controlled to be incident at an angle equal to or greater than about 41.4 degrees such that the light is totally reflected from the glass of the vehicle 10.

The light receiving unit 130 may include a light receiving module 131 for receiving light and a light receiving saw-toothed rotational prism set 132.

The light receiving module 131 is a means for receiving light, wherein the light corresponds to that reflected from the windshield glass and the frost sensing region 111, and the light receiving module receives the light and outputs a signal corresponding to the received light to the control unit 140.

In order for the light totally reflected from the glass of the vehicle 10 to be received by the light receiving module 131, the light receiving saw-toothed rotational prism set 132 deflects the light to the light receiving module 131 to be received.

That is, the light receiving saw-toothed rotational prism set 132 guides the light incident in parallel such that the light transmits the prism thereof and then it is concentrated at maximum to a point. Therefore, the light receiving saw-toothed rotational prism set 132 is preferably designed in such a manner that the region on which light is concentrated through the prism becomes the light receiving module 131.

In this case, the light receiving saw-toothed rotational prism set 132 is configured to be symmetrical with the light emitting saw-toothed rotational prism set 123 on the basis of a central line in any vertical direction.

In addition, since the light emitting module 121 can be made up of two or more modules depending on design conditions of the present invention, the light receiving saw-toothed rotational prism set 132 may be configured to rotate (or control) the direction of the prism such that the light emitted from each of the light emitting modules 121 can be totally reflected from the glass of the vehicle 10 and received by a single light receiving module 131. Here, the 'rotate' means 'control of a direction' rather than 'turning about an axis.'

The control unit 140 receives the signal output from the light receiving module 131, and may send a control signal to the vehicle through communication with the vehicle.

In this case, the communication with the vehicle can be made through LIN communication.

Since LIN (Local Interconnect Network) communication is used for data transfer between an ECU of vehicles and an active sensor and an active actuator, it is preferably applied to the present invention for sensing raindrops and operating a wiper and an air conditioning system of vehicles actively.

In addition, the control unit is capable of identifying whether raindrops W and frost F exist by analyzing the received signal, and sending appropriate control signals to the vehicle based on the types and amount of substances detected and the cycle of raindrops. The control unit controls the wiper and the air conditioning system of the vehicle to remove the raindrops W and frost F.

The air conditioning system is capable of removing the frost F and may include a heater in vehicles and a heating wire embedded in the windshield glass. Therefore, the control unit activates the air conditioning system in response to the signal output from the light receiving module 131 to remove the frost F.

In addition, the control unit may set a threshold value based on data regarding an amount of light received due to raindrop W and frost F, and determines the signal received from the light receiving module 131 based on the threshold value and outputs a control signal for activating the wiper or the air conditioning system.

In this case, the threshold value indicates the minimum value with respect to the amount of raindrops and frost to activate the wiper and the air conditioning system. That is, if the amount of raindrops W and frost F is less than a predetermined threshold value, the control unit does not activate the wiper or the air conditioning system of the vehicle, so that unnecessary operation of the wiper is minimized FIG. 4 illustrates schematically a movement path of light according to an internal configuration and operation of a rain sensor having the frost sensing function according to another embodiment of the present invention.

Figure 4:
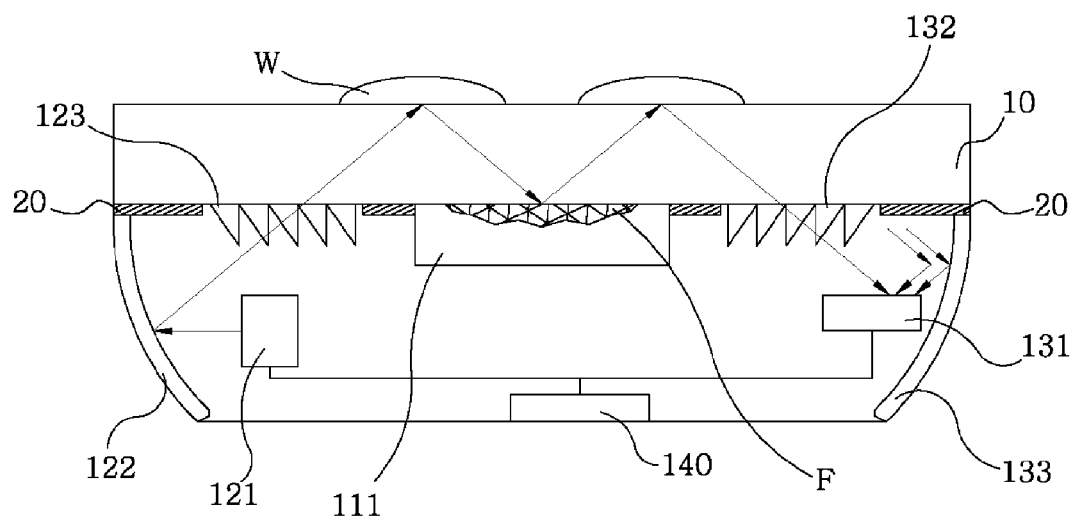
FIG. 4 is a schematic view showing a movement path of light according to an internal configuration and operation of the rain sensor having the frost sensing function according to another embodiment of the present invention.

Referring to FIG. 4, the light receiving unit 130 may further include a light receiving parabolic mirror module 133.

The light receiving parabolic mirror module 133 has a reflection surface of a paraboloid shape to reflect the light coming out of the light receiving module 131, among the light totally reflected from the glass of the vehicle 10 and the frost sensing area 111 after being emitted from the light emitting module 121, to the light receiving module 131.

As shown in FIG. 4, the present invention is configured to be able to receive the light totally reflected from the glass of the vehicle 10 more efficiently so that the sensing function is enhanced.

FIGS. 5*a* to 5*d* are schematic views showing light varying as the rain sensor having the frost sensing function according to an embodiment of the present invention detects at each of sensing regions, and FIG. 6 is a schematic view showing light varying as the rain sensor having the frost sensing function according to an embodiment of the present invention detects at a plurality of sensing regions.

In this case, regarding arrow lines shown in FIGS. 5*a* to 5*d* and 6*a* to 6*d*, a solid arrow line means the amount of light emitted from the light emitting module 121, a one-dot chain arrow line means the amount of light that some of the light indicated by the solid line is lost, and a broken arrow line means the amount of light that some of the light indicated by the one-dot chain line is lost. Here, the smaller the distance is between each of broken lines in the arrow lines and the denser the broken lines are, the less amount of the light is.

Figure 5A:
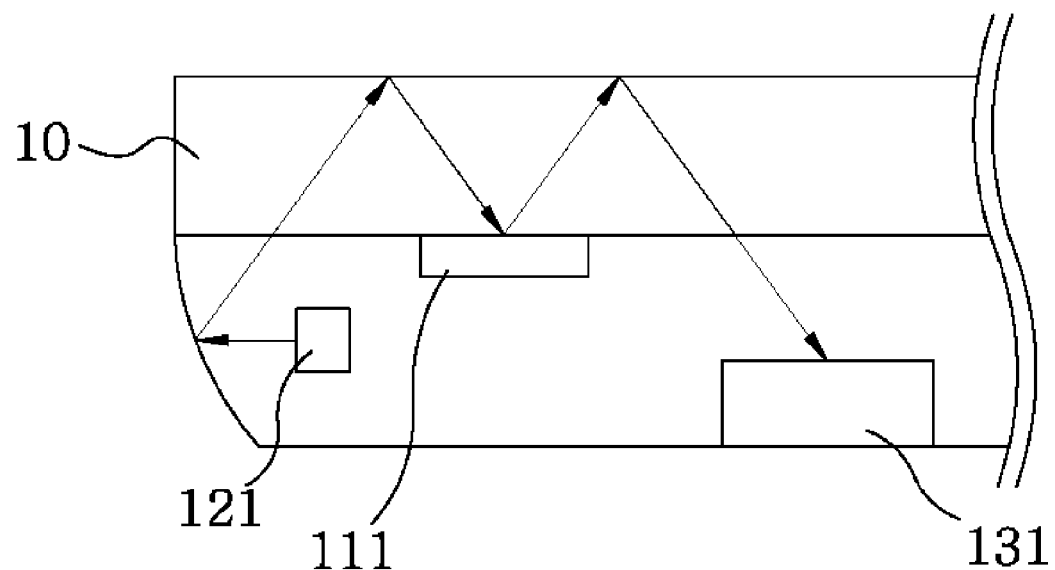
FIGS. 5a to 5d are schematic views showing light varying as the rain sensor having the frost sensing function according to an embodiment of the present invention detects at each of sensing regions.

FIG. 5*a* of the accompanying drawings illustrates a movement path of light that the light emitted from the light emitting module 121 is totally reflected from the windshield glass and the frost sensing region 111 and then received by the light receiving module 131 when there is no substance detected on windshield glass.

At this time, as the light emitted from the light emitting module 121 is incident on the windshield glass at an angle exceeding the critical angle, the incident light is totally reflected from the windshield glass and the frost sensing region 111 and then received by the light receiving module 131. In this case, as the light received by the light receiving module 131 is received through total reflection, its amount is equal to that of the light emitted from the light emitting module 121.

Therefore, when the amount of the light received by the light receiving module 131 is equal to that of the light emitted from the light emitting module 121, no control signal is output such that the wiper and the air conditioning system of the vehicle does not operate.

Figure 5B:
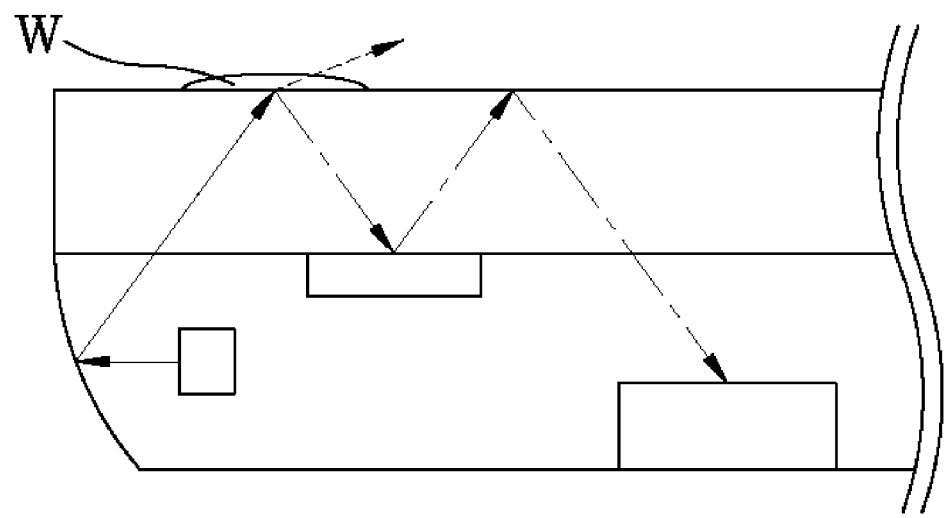
Figure 5C:
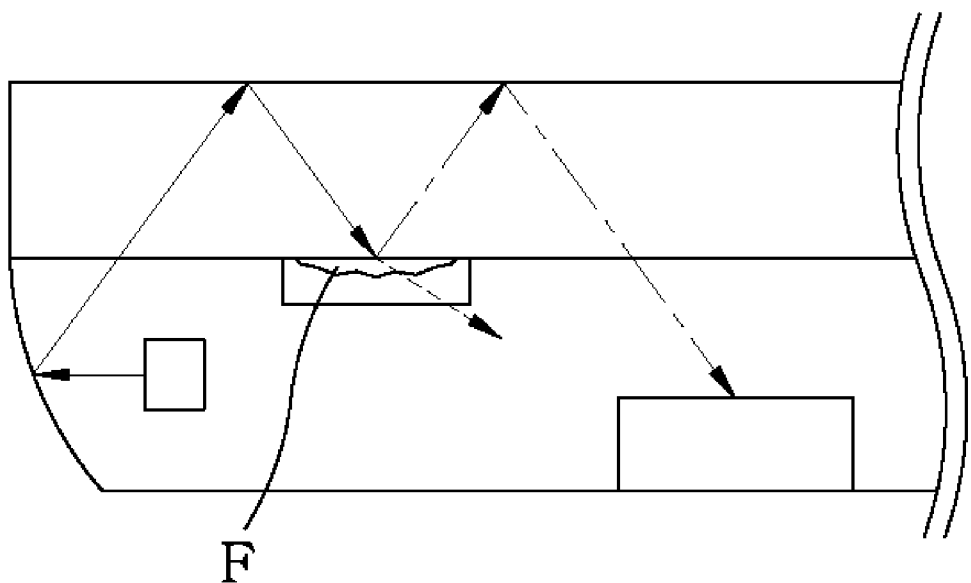
Figure 5D:
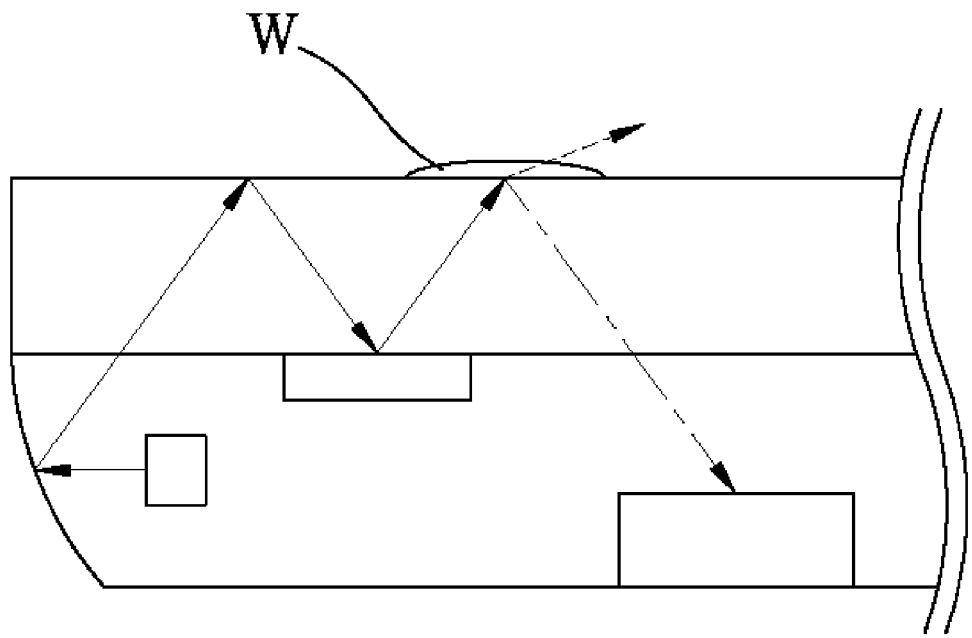

Referring to FIGS. 5b to 5d of the accompanying drawings, if the light emitted from the light emitting module 121 is incident on the region to which raindrops W or frost F adhere at an angle equal to or greater than the critical angle when sensing the raindrops W or the frost F, some of the light is transmitted to the outside or lost through the raindrops W or the frost F having refractive index greater than that of air.

Therefore, the light receiving module 131 analyzes the amount of light being received, and detects the raindrops W or the frost F and then outputs a signal accordingly.

At this time, although the amount of light being received in FIGS. 5b and 5d and the amount of light being received in FIG. 5c are shown as the same one-dot chain line, since amounts of light that are lost through the actual raindrops W and the frost F are different, the light receiving module 131 outputs signals differently due to such a difference between the amounts.

Figure 6A:
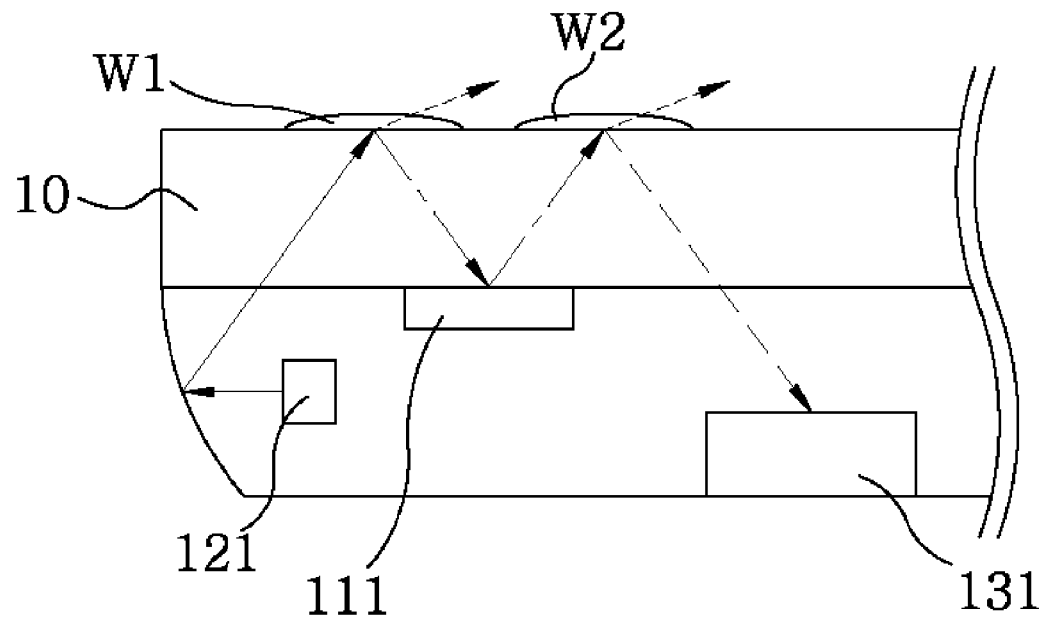
FIGS. 6a to 6d are schematic views showing light varying as the rain sensor having the frost sensing function according to an embodiment of the present invention detects at a plurality of sensing regions.

Referring to FIG. 6a of the accompanying drawings, it illustrates schematically variation of the amount of light upon sensing a large amount of raindrops W1 and W2.

When the light emitted from the light emitting module 121 is reflected by raindrops W1, some of the light is transmitted to the outside or lost while the other light is reflected to the frost sensing region 111. The light is totally reflected from the frost sensing region 111 and then reflected toward the direction of raindrops W2 while some of the light is lost by the raindrops W2 and the other light is received by the light receiving module 131.

Therefore, the light receiving module 131 analyzes the amount of light being received, detects the large amount of raindrops W1 and W2, and then outputs a signal accordingly.

Figure 6B:
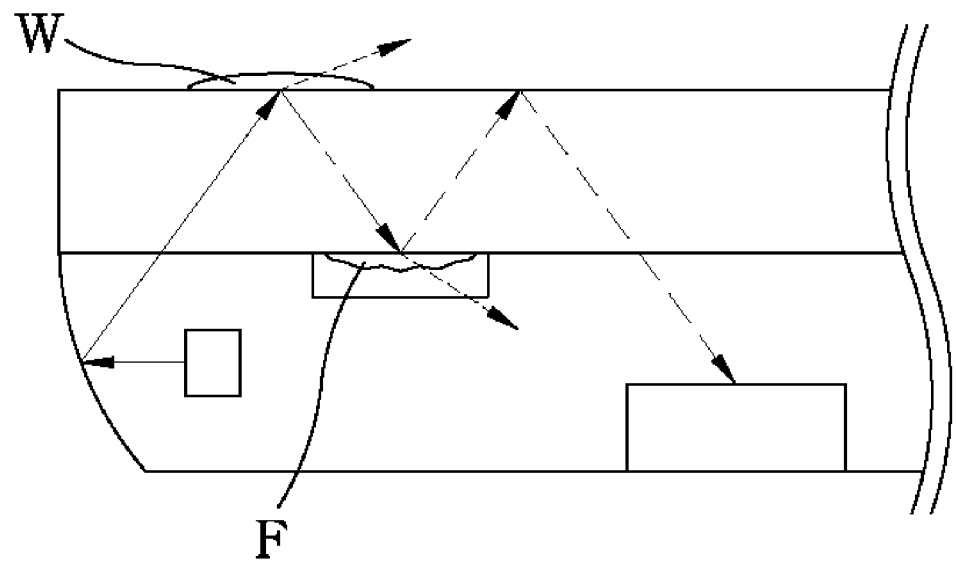
Figure 6C:
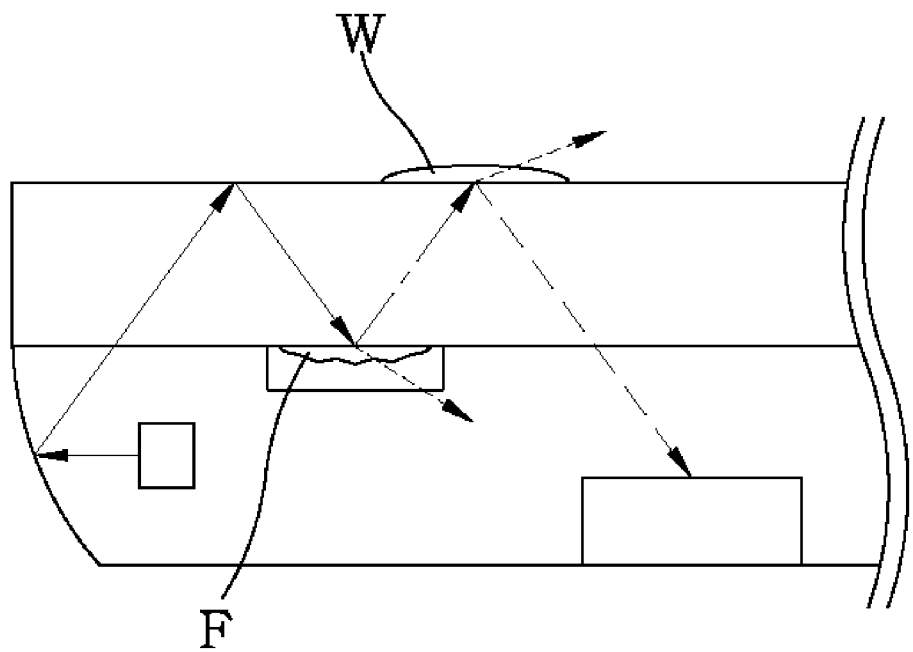

Referring to FIGS. 6b and 6c of the accompanying drawings, they illustrate schematically variation of the amount of light upon sensing raindrops W and frost F.

While the raindrops W and frost F are detected by the light emitted from the light emitting module 121, some of the light is lost and the other light is received by the light receiving module 131.

Therefore, the light receiving module 131 analyzes the amount of light being received, and detects the raindrops W and the frost F and then outputs a signal accordingly.

At this time, although the amount of light being received in FIG. 6a and the amount of light being received in FIGS. 6b and 6c are shown as the same broken line, since amounts of light that are lost through the actual raindrops W, W1 and W2 and the frost F are different, the light receiving module 131 outputs signals differently due to such a difference between the amounts.

Figure 6D:
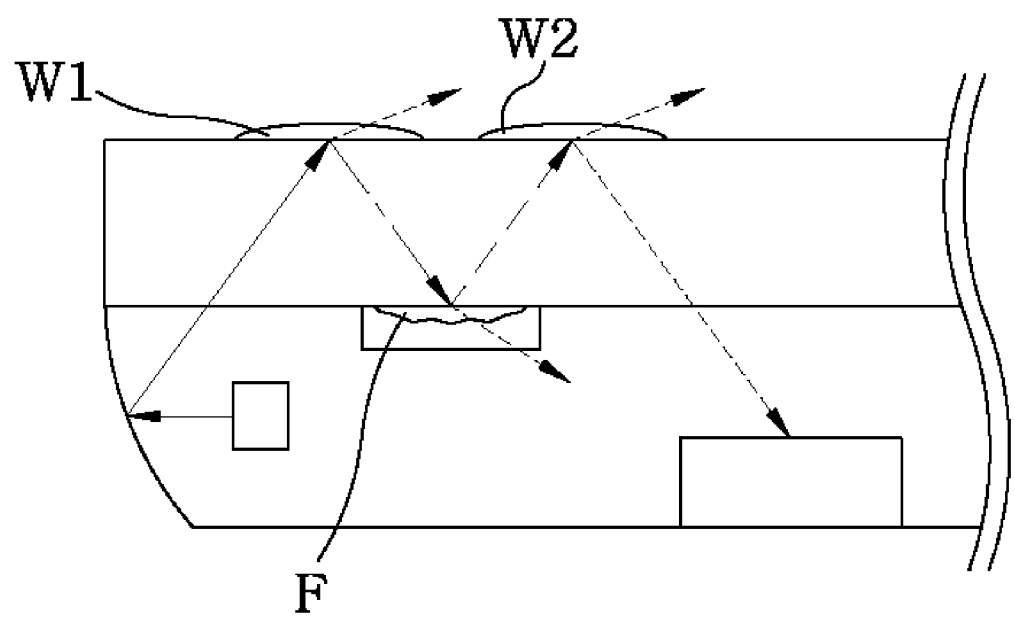

Referring to FIG. 6d of the accompanying drawings, it illustrates schematically variation of the amount of light upon sensing a large amount of raindrops W1 and W2 and frost F.

While the large amount of raindrops W1 and W2 and frost F are detected by means of the light emitted from the light emitting module 121 at every sensing region, some of the light is lost and the remaining light is received by the light receiving module 131.

Therefore, the light receiving module 131 analyzes the amount of light being received, and detects the large amount of raindrops W1 and W2 and frost F and then outputs a signal accordingly.

Classification of the magnitude of signals depending on raindrops W and frost F as discussed in the foregoing is an exemplary example. Alternatively or additionally, it is also possible to establish database for various situations and further utilize it in signal analysis.

Through the configuration and process mentioned above, the rain sensor according to the present invention has a function to detect the frost by modifying only the structure of a rain sensor without a need to additionally include a separate sensor, and thus there is no additional cost.

The invention has been described in detail with reference to preferred embodiments thereof. However, it will be appreciated by those skilled in the art that the scope of the present invention is not limited to the embodiments as mentioned above and that changes may be made in these embodiments without departing from the principles and spirit of the invention, the scope of which is defined in the appended claims and their equivalents.

What is claimed is:

1. A rain sensor having a frost sensing function, the rain sensor being attached to a windshield glass of a vehicle, comprising:
    a casing provided with a frost sensing region and an air passage formed by recessing a part of a surface of the casing which is attached to the windshield glass to contact indoor air of the vehicle;
    a light emitting unit configured to emit light such that the light is totally reflected from an exterior side surface of the windshield glass and the frost sensing region;
    a light receiving unit that receives the light reflected totally and outputs signals; and
    a control unit that receives the signals from the light receiving unit and analyzes a condition of raindrops on the exterior side surface of the glass and a condition of frost generated on an interior side surface of the windshield glass,
    wherein the air passage is formed by recessing a same surface as the frost sensing region, and connects an interior of the vehicle and the frost sensing region such that the indoor air is introduced into the frost sensing region through the air passage.

2. The rain sensor of claim 1, wherein the control unit outputs a control signal to control a wiper and an air conditioning system of the vehicle depending on results of analyzing the conditions of raindrops and frost.

3. The rain sensor of claim 1, wherein the light emitting unit comprises:
    a light emitting module for emitting light;
    a light emitting parabolic mirror module having a reflection surface of a paraboloid shape to reflect in parallel the light emitted from the light emitting module and allowing the light to be reflected to the windshield glass; and
    a light emitting saw-toothed rotational prism set allowing the light reflected from the light emitting parabolic mirror module to be transmitted in parallel.

4. The rain sensor of claim 3, wherein the light emitting parabolic mirror module reflects the light emitted from the light emitting module such that the light is incident on the windshield glass at an angle that allows the light to be totally reflected from the windshield glass.

5. The rain sensor of claim 1, wherein the light receiving unit comprises:
a light receiving module for receiving the light emitted from the light emitting module and then totally reflected from the windshield glass; and
a light receiving saw-toothed rotational prism set through which the light totally reflected from the windshield glass is transmitted.

6. The rain sensor of claim 5, wherein the light receiving unit comprises a light receiving parabolic mirror module having a reflection surface of a paraboloid shape.

7. The rain sensor of claim 1, wherein the light emitting unit comprises two or more light emitting units so that two or more sensing regions for sensing raindrops exist.

* * * * *